United States Patent [19]

Montgomery et al.

[11] Patent Number: 5,384,310

[45] Date of Patent: * Jan. 24, 1995

[54] 2'-FLUORO-2-HALOARABINOADINOSINES AND THEIR PHARMACEUTICAL COMPOSITIONS

[75] Inventors: John A. Montgomery; John A. Secrist, III, both of Birmingham, Ala.

[73] Assignee: Southern Research Institute, Birmingham, Ala.

[*] Notice: The portion of the term of this patent subsequent to Jul. 23, 2008 has been disclaimed.

[21] Appl. No.: 693,646

[22] Filed: May 10, 1991

Related U.S. Application Data

[63] Continuation-in-part of Ser. No. 355,358, May 23, 1989, Pat. No. 5,034,518.

[51] Int. Cl.$^6$ .................. A61K 31/70; C07H 19/19
[52] U.S. Cl. .................. 514/46; 536/27.4; 536/27.63
[58] Field of Search .................. 536/24, 26; 514/45, 514/46

[56] References Cited

U.S. PATENT DOCUMENTS

| | | | |
|---|---|---|---|
| 4,188,378 | 2/1980 | Montgomery | 536/26 |
| 4,751,221 | 6/1988 | Watanabe et al. | 514/46 |
| 4,918,179 | 4/1990 | Watanabe et al. | 536/26 |

FOREIGN PATENT DOCUMENTS

| | | |
|---|---|---|
| 314011 | 10/1988 | European Pat. Off. . |
| 8908658 | 9/1989 | WIPO . |

OTHER PUBLICATIONS

"9-(2-Deoxy-2-fluoro-βD-arabinofuranosyl)guanine", Montgomery et al. J. Med. Chem. 29 (1986) 2389–2392.

*Primary Examiner*—John W. Rollins
*Assistant Examiner*—L. Eric Crane
*Attorney, Agent, or Firm*—Yahwak & Associates

[57] ABSTRACT

The present invention is directed to certain 2'-fluoro, 2-substituted purine nucleosides which are toxic to cancerous cell lines.

10 Claims, No Drawings

2'-FLUORO-2-HALOARABINOADINOSINES AND THEIR PHARMACEUTICAL COMPOSITIONS

This application is a continuation-in-part of U.S. patent application Ser. No. 07/355,358, filed May 23rd 1989.

The research leading to the discovery of the present invention was funded, in part, by funds from the United Stated Department of Health and Human Services. Accordingly, the United States government has certain statutory rights to the present invention under 37 USC 200 et seq.

The development of effective anticancer agents is a complex problem for a number of reasons, but primarily because of the lack of an identifiable, exploitable biochemical difference between normal and malignant tumor cells, be they of animal or human origin.

The simplest and most used strategy for the discovery of new anticancer agents is by empirical search, which has been most successful in identifying useful antitumor antibiotics. The search for lead compounds among synthetics is somewhat different, since few clinically useful agents have resulted from strictly random screening, which in fact is not a truly random search since it reflects the status of organic chemistry and, largely, what synthetic chemists have found of interest for whatever reason. In fact, most synthetics found to have clinical activity were screened for a reason. A prime example is one of the first clinically useful agents, nitrogen mustard, which was tested because of its effects on the blood elements discovered in the chemical warfare program. Regardless of the method of discovery, anticancer agents can be classified in five broad groupings:

A. Antimetabolites
   Glutamine antagonists
   Inhibitors of dihydrofolic reductase
   Purine and pyrimidine analogs
   Nucleoside diphosphate inhibitors
B. Nucleic acid complexors
   Actinomycins
   Anthracyclines
   Bleomycins
   Mitomycins
   Mithramycin
   Neocarcinostatin
   Anthramycins
C. Chemically reactive compounds
   Nitrogen mustards
   Aziridines
   Sulfonates
   Triazenes
   Nitrosoureas
   Procarbazine
   cis-Platinum
D. Mitotic inhibitors
   Vinca alkaloids
   Podophyllum derivatives
E. Hormones
   Estrogens
   Androgens
   Progestogens
   Glucocorticoids
   Miscellaneous synthetics From these groupings, it is clear that anticancer agents with proven utility interfere one way or another with cell division and, since cancer cells must divide or eventually die, they are cytotoxic agents with some degree of specificity for neoplastic cells. Thus it would seem logical that the search for new lead compounds should focus on new structural types that will also interfere with one or another of the processes of cell division. The most approachable of these is the design of enzyme inhibitors. There are at least 85 enzymatic reactions involved in the de novo synthesis of purine and pyrimidine nucleotides, in their interconversion, in their polymerization to nucleic acids, and in the so called salvage pathways. Of these 85 enzymes, approximately 14 are known to be inhibited by metabolic analogs or anabolites thereof. These inhibitions are thought to be responsible for, or at least contribute to, the anticancer activity of these compounds.

Two such compounds are the arabinofuranosyl nucleosides, 9-β-D-arabinofuranosyladenine and 1-β-D-arabinofuranosylcytosine, of the formula:

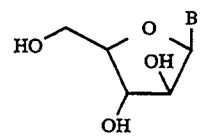

wherein B is adenine or cytosine, have well-known antiviral (B=adenine) and anticancer (B=cytosine) activity. In addition, other arabinofuranosyl nucleosides with 2'-substituents other than hydroxyl have also exhibited useful biological effects. All of these nucleosides require activation (phosphorylation) to be effective, and generally this is accomplished by different enzymes than the corresponding ribofuranosyl nucleosides.

In addition, a number of 2'-substituted-9-β-D-arabinofuranosyl-2-haloadenines [see J. Med. Chem. 31:405 (1988), and J. Med. Chem. 29:2389 (1986)] have also been developed along this general design. 9-β-D-arabinofuranosyl-2-fluoroadenine monophosphate is, for example, is a drug of choice against chronic lymphocytic leukemia; and 2-chloro-2'-deoxyadenosine has shown some promise in a phase 1 trial against T-cell neoplasms and in phase II trials against chromic lymphocytic leukemia of B-cell origin that is refractory to conventional therapy, and against hairy-cell leukemia. However, the search for better and more effective, anticancer compounds continues.

Thus, in accordance with the present invention it has now been found that the incorporation of a 2-halo substituent onto the purine ring of these prior compounds significantly alters the metabolism of adenine nucleosides, specifically by reducing the ability of the compound to serve as a substrate for adenosine deaminase; that substituting a fluorine in the arabino configuration at C-2' makes these derivatives highly resistant to phosphorolytic cleavage; and that the combination of these two changes in the same molecule provide enhanced biological and anti cancer activity of the resulting compound.

The present invention relates to a family of novel nucleoside compounds, and pharmaceutically acceptable salts thereof, represented by the general formula:

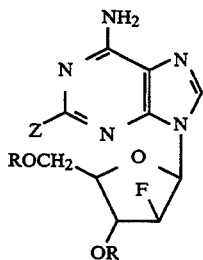

in which R, which may be the same or different, is a hydrogen or acyl protecting group such as an alkanoyl protecting or blocking group such as benzoyl, and wherein Z is a halogen of the group F, Cl, and Br. In accordance with one aspect of the present invention, where R is acyl, the nucleoside compound acts as a prodrug in prolonging the in vivo life of the compound.

More specifically, the most preferred compounds of the present invention are those of formula:

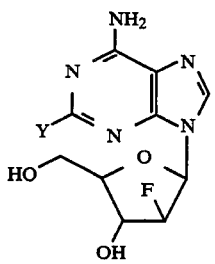

wherein Y is F, Cl or Br, or the pharmaceutically acceptable salts thereof.

This and other aspects of the present invention will become clearer in the following discussion and description, both provided for purposes of clarification and not limitation as to the scope of the present invention.

In its broadest description, 2'-substituted purine arabinonucleosides are prepared from 2-haloadenosines via their 3',5'-O-(tetraisopropyldisiloxane-2'-O-triflate derivatives according to the process discussed in J. Med. Chem. 31:405 (1988). Since this prior approaches failed to provide the 2'-fluoroarabinonucleosides in reasonable yields, these compounds had to be prepared by reaction of the appropriately blocked 2'-fluoro sugar (compound 1) with 2,6-dichloropurine followed by modification of the purine [see J. Med. Chem. 29:2389 (1986)].

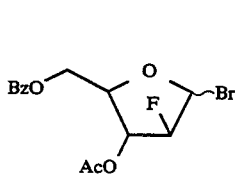

1

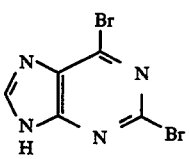

2

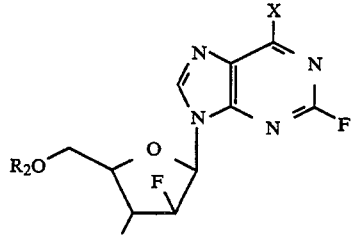

3

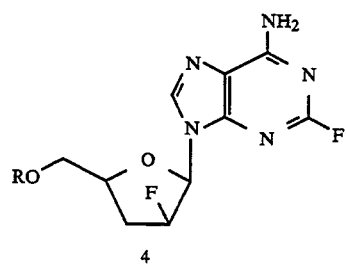

4 a) X = Y = Br, R₁ = Ac, R₂ = Bz
b) X = NH₂, Y = Br, R₁ = R₂ = H
c) X = Y = Cl, R₁ = Ac, R₂ = Bz
d) X = NH₂, Y = Cl, R₁ = R₂ = H
e) X = Y = NH₂, R₁ = Ac, R₂ = Bz
f) X = NH₂, Y = F, R₁ = Ac, R₂ = Bz
g) X = NH₂, Y = F, R₁ = R₂ = H
h) X = NH₂, Y = F, R₁ = H, R₂ = Bz a) R = Bz
b) R = H

The same sequence was also applied to 2,6-dibromopurine (compound 2) for the preparation of the 2-bromoadenine nucleoside. The blocked 2'-fluoro sugar was condensed with 2,6-dibromopurine in refluxing 1,2-dichloroethane in the presence of 4A molecular sieves. The anomeric configuration and substitution positions for compound 3a were confirmed by ¹H NMR comparisons with compound 3c. Amination and deprotection of compound 3a or 3c done in ethanolic ammonia yielded a mixture of the desired product and the 5'-benzoyl protected compound. This residual blocking group may be removed if desired by treating the mixture with LiOH in MeCN—H₂O to give either compound 3b or 3d.

Non-aqueous diazotization of compound 3e with tert-butylnitrite in 60% hydrogen fluoride/pyridine at −20° C. produced the 2-fluoro compound 3f. Deacylation of compound 3f was accomplished with LiOH in MeCN—H₂O, allowing a reasonable yield of compound 3g, free of any side products.

In order to prepare the dideoxy compound 4b, the 3'-acetyl of compound 3f was first selectively removed with NaHCO₃ in MeOH. The resulting product, compound 3h, was then treated with thiocarbonyldiimidazole followed by reduction with tri-n-butyltin hydride to give compound 4a. The 5'-benzoyl protecting group of compound 4a was then removed with LiOH to produce compound 4b.

The following examples, given for purposes of clarity in more fully demonstrating the methods by which the compounds of the present invention may be prepared, are provided. However, these examples are not meant to be limiting in any manner, and modifications and adaptions may be made to provide other routes, which are to be considered to be within the scope of the present invention, for the synthesis of the desired compounds.

EXAMPLE I 2,6-Dibromo-9-(3-O-acetyl-5-O-benzoyl-2-deoxy-2-fluoro-β-D-arabinofuranosyl)-9H-purine (compound 3a)

A solution of 3-acetyl-5-benzoyl-2-deoxy-2-fluoroarabinofuranosylbromide (33.2 mmol) in 400 mL of dry dichloroethane was stirred for 10 min with 4A molecular sieves (250 mL) before the addition of (9.3 g, 33.5 mmol) 2,6-dibromopurine. The mixture was vigorously stirred with an overhead stirrer and placed in a preheated 100° C. oil bath. Heating was continued for 32 h until all the bromosugar was consumed. (TLC 2:1 cyclohexane-ethyl acetate, using 4-(4-nitrobenzyl) pyridine spray for detection.) After the mixture had cooled to room temperature, it was filtered through Celite. The solids were washed with dichloroethane, and the combined filtrates were evaporated to dryness in vacuo. The residue (16.5 g) was a mixture of three nucleosides which were separated by flash chromatography on 150 g of silica gel (230–400 mesh) using 2:1 cyclohexane-ethyl acetate as the eluting solvent. By combining pure fractions, the desired compound was obtained as a glass 3.64 g (19.7%) which was chromatographically homogeneous but would not crystallize. A second column run on impure fractions gave 2.21 g (11.9%) more pure product for a total yield of 31.6%.

EXAMPLE II

2-Bromo-9-(2-deoxy-2-fluoro-β-D-arabinofuranosyl)-9H-purin-6-amine (compound 3b)

A solution of the example I product (5.84 g, 10.5 mmol) in 400 mL of ethanolic ammonia (saturated at 0° C.) was sealed in a glass-lined stainless steel bomb and left at room temperature for 3 days. The solution was evaporated to dryness and evaporated with ethanol to remove ammonia. The residue, containing the desired product and 5'-benzoyl compound, was dissolved in 440 mL of acetonitrile and 120 mL of water. Lithium hydroxide monohydrate (881 mg, 21 mmol) was added, and the solution was stirred for 16 h at room temperature. Thin-layer chromatography (5:1 CHCL$_3$—MeOH) indicated complete reaction. The chilled solution was carefully neutralized with glacial acetic acid and evaporated to dryness. The white solid residue was recrystallized from water. The product was dried in vacuo at room temperature at 100° C. for 2 h: 2.15 g (59.2%); Mp 209°–210° C.

EXAMPLE III

2-Chloro-9-(2-deoxy-2-fluoro-β-D-arabinofuranosyl)-9H-purin-6-amine (compound 3d)

A solution of the compound 3c [see J. Med. Chem. 29:2389 (1986)] (5.1 g, 10.9 mmol) in ethanol saturated (0° C.) with anhydrous ammonia (100 mL) was placed in a glass-lined stainless steel bomb and left at room temperature for three days. Thin layer chromatography (2:1 cyclohexane-ethyl acetate and 5:1 CHCl$_3$—MeOH) indicated the absence of starting material. However, two major products were present: the desired compound and its 5'-benzoyl analog. The solution was evaporated to dryness and co-evaporated with acetonitrile. The residue was dissolved in acetonitrile (100 mL) and diluted with water (60 mL) before the addition of lithium hydroxide monohydrate (915 mg, 21.8 mmol). The solution was stirred at room temperature for 3 h, at which time thin layer chromatography (5:1 CHCl$_3$—MeOH) indicated the reaction had gone to completion. The solution was cooled, neutralized with acetic acid, and evaporated to dryness. Three recrystallizations from water gave the pure compound: 1.4 g (42.3%); Mp 225°–226° C.

EXAMPLE IV

2-Fluoro-9-(3-O-acetyl-5-O-benzoyl-2-deoxy-2-fluoro-β-arabinofuranosyl)-9H-purin-6-amine (compound 3f)

Diamino compound 3e [see J. Med. Chem. 29:2389 (1986)] (700 mg, 1.63 mmol) was dissolved in 3:2 HF-pyridine (15 mL) at −25° C. and treated with tert-butylnitrite (271 μL, 2.28 mmol). After 1 h at −20° C., the reaction was incomplete as indicated by thin layer chromatography. Additional tert-butylnitrite (70 μL, 0.59 mmol) was added, and the reaction was held at −20° C. for an additional 2 h. The cold reaction solution was added dropwise to saturated aqueous NaHCO$_3$ (1 L) containing ice. The foaming mixture was stirred vigorously for 20 min, then diluted with CHCl$_3$ (300 mL). The solution was allowed to layer, and the layers were separated, and the aqueous layer was extracted with additional CHCl$_3$ (2×175 mL). The combined organic extracts were washed with water (3×175 mL), dried (over MgSO$_4$), and evaporated to dryness. The resulting residue, in CHCl$_3$, was applied to a flash column containing 50 g of silica gel (230–400 mesh) with CHCl$_3$ as eluant. Fractions were combined to give essentially pure product (500 mg, 70%). Crystallization of a small sample from EtOH gave pure product: Mp 208°–209° C.

EXAMPLE V

2-Fluoro-9-(2-deoxy-2-fluoro-β-D-arabinofuranosyl)-9H-purin-6-amine (compound 3g)

A suspension of the example IV product (430 mg, 0.99 mmol) in 1:1 MeCN—H$_2$O (40 mL) was treated in one portion with solid lithium hydroxide monohydrate (125 mg, 2.97 mmol). The reaction became a clear solution after being stirred at room temperature for 20 min. A 3 h thin layer chromatography aliquot showed the deblocking to be complete. Glacial acetic acid (57 μL) was added, and the solution was evaporated until a white solid was deposited. After being chilled, the solid was collected, washed with cold water, and dried in vacuo at room temperature to give a crude solid (252 mg). This solid was dissolved in 40 mL of water and applied to a water-equilibrated SM-4 Bio-Bead column (1.5×32 cm). After initial elution with water, the product was eluted with a step-wise gradient, 5% →20% EtOH in water. The residue from the combined evaporated column fractions was crystallized from 25 mL of boiling water with charcoal treatment, and dried in vacuo at 56° C. for 16 h to yield a pure product: 178 mg (59%); Mp 207°–209° C.

EXAMPLE VI

2-Fluoro-9-(5-O-benzoyl-2-deoxy-2-fluoro-β-D-arabinofuranosyl)-9H-purin-6-amine (compound 3h)

A suspension of the example IV product (312 mg, 0.72 mmol) in MeOH (25 mL) at 10° C. was treated with solid NaHCO$_3$ (181 mg, 2.16 mmol). After being stirred at room temperature for 2.5 h, the reaction was quenched by the addition of glacial acetic acid (170 μL)

and evaporated to dryness. This residue in hot EtOH was applied to two silica gel thick plates (A, naltech, GF, 2000 μm) and subsequently developed in 9:1 CHCl$_3$—MeOH. The product was extracted with hot EtOH and evaporated to dryness to give essentially pure product: 208 mg (74%).

EXAMPLE VII

2-Fluoro-9-(5-O-benzoyl-2,3-dideoxy-2-fluoro-β-D-arabinofuranosyl)-9H-purin-6-amine (compound 4a)

191 mg (0.49 mmol) of the compound made in accordance with example VI was dissolved in dry acetonitrile (20 mL) at 45° C., and then treated with 1,1'-thiocarbonyldiimidazole (339 mg, 1.7 mmol). The resulting cloudy yellow solution was stirred under N$_2$ at 45° C. for 24 h at which time thin layer chromatography analysis (EtOAc) showed one major product. The reaction was evaporated to dryness, and the residue was dissolved in dry toluene (15 mL). Treatment with AIBN (13.7 mg, 0.08 mmol) and tri-n-butyltin hydride (1.3 mL, 4.7 mmol) produced a yellow mixture that was placed directly in a 120° C. bath. A clear solution was observed after a 5 min reflux, and at 1 h the reaction was complete as indicated by thin layer chromatography. The solvent was then removed in vacuo, and the resulting syrup was coevaporated once with EtOH. Trituration of this residue with petroleum ether (50 mL) produced a white solid that was collected and washed with fresh solvent to give 214 mg of crude solid. This material in hot EtOH was applied to two Analtech (GF, 2000 μm) layer plates. After three developments in 9:1 CHCl$_3$—MeOH, the product band was extracted with boiling EtOH. The residue from evaporation of the combined extracts was crystallized from boiling EtOH to yield sufficiently pure product 160 mg (87%); Mp 215°–217° C.

Without any further purification, this material was used in the deprotection step of example VIII.

Example VIII

2-Fluoro-9-(2-3-dideoxy-2-fluoro-β-D-arabinofuranosyl)-9H-purin-6-amine (compound 4b)

A suspension of the example VII compound (135 mg, 0.36 mmol) in 3:1 MeCN—H$_2$O was treated in one portion at room temperature with solid LiOH·H$_2$O (38 mg, 0.9 mmol). The stirred mixture became a clear solution after ½ h. At 7 h an aliquot examined by TLC (5:1 CHCl$_3$—MeOH) showed the absence of the example VII compound. Glacial acetic acid (35 μL) was added, and the reaction was evaporated to dryness. This residue in hot acetonitrile was applied to one silica gel thick plate (Analtech, GF, 2000 μm). After the plate was developed three times in 5:1 CHCl$_3$—MeOH, the product band was extracted with boiling MeCN. Evaporation of this extract gave slightly impure material that was chromatographed as above on three prep plates (Analtech, GF, 1000 μm). The resulting residue was crystallized from boiling H$_2$O (25 mL) containing EtOH (0.5 mL). After being chilled, the white solid was collected, washed with cold H$_2$O and dried in vacuo at 56° C. for 16 h to give pure product, 71 mg (73%); Mp 249°–250° C.

In contrast to the previously reported 2'-substituted 9-β-D-arabinofuranosyl-2-haloadenines, the 2'-fluoro compounds were quite cytotoxic to three human cell lines, H.Ep.-2, CCRF—CEM, and K562, and the murine lukemia line, L1210. They, in fact, are significantly more cytotoxic than the corresponding 9-β-D-arabinofuranosyl-2-haloadenines, resembling more closely the 2'-deoxy-2-halodenosines (see Table 1).

Obviously, to be useful as anticancer agents, the nucleosides of the present invention must show the ability to kill cells in vitro. The results in Table I, indicating the concentration required to inhibit cell proliferation to 50% of untreated controls, show that these nucleosides can, at reasonable concentrations, kill cells. One cell line (L1210) is a murine lukemia, whereas the other three are human neoplasms. Based on many years of experience, we believe that compounds that do not require activation by the liver must have an IC$_{50}$ of about 1–10 μM or less to show useful activity in the in vivo animal models—and in man. Many people today emphasize the importance of toxicity to human cell lines.

TABLE I

Cytotoxicity [as IC$_{50}$ (μM)] of 2-Haloadenine Nucleosides

| Compound | H.Ep.-2 | L1210 | CCRF-CEM | K562 |
|---|---|---|---|---|
| when Y = F | | | | |
| X = OH | 9 | 3 | 0.4 | 0.15 |
| X = H | 0.2 | 0.9 | 0.2 | |
| X = F | 0.34 | 0.38 | 0.14 | 0.3 |
| when Y = Cl | | | | |
| X = OH | 3 | <3 | 10 | |
| X = H | 0.03 | 0.07 | 0.003 | |
| X = F | 0.012 | 0.23 | 0.05 | 0.003 |
| when Y = Br | | | | |
| X = OH | 4 | 3 | | |
| X = H | 0.02 | 0.9 | 0.02 | |
| X = F | 0.22 | 0.26 | 0.02 | 0.05 |

The data in Table I (given in μM amounts) clearly establishes the ability of the compounds according to the present invention to kill neoplastic cells.

Subsequently, the phosphorolysis of these compounds were compared by *E. coil* purine nucleoside phosphorylase. The arabino and 2'-deoxyribonucleosides are rapidly cleaved by this enzyme, whereas the arabino nucleosides substituted at 2' by Cl, N$_3$, or NH$_2$ are almost completely resistant., The 2'-fluoro compounds are less resistant to cleavage, being cleaved at roughly one-third the rate of the arabino and 2'-deoxynucleosides. This reduction in cleavage rate may be acceptable for pharmaceutical purposes as phosphorylation in mammalian cells is quite rapid.

More specifically, an enzyme reaction mixture consisting of 0.5 mM nucleoside substrate, 50 mM pH 8.0 phosphate buffer and purine nucleoside phosphorylase in a final volume of 1.0 mL was allowed to incubate for 30, 60, 120, 180 and 240 minutes, and the amounts of nucleoside and substrate remaining were determined by HPLC. The results of this experiment are tabulated in the following Table II.

TABLE II

Phosphorolysis of Nucleosides

| Compound | % Cleavage |
| --- | --- |
| 3b | 45 |
| 3d | 39 |
| 3g | 10 |
| 2-fluoro-9-β-D-arabinofuranosyladenine | 99 |
| 2-chloro-2'-deoxyadenosine | >99 |
| 2-fluoro-2'-deoxyadenosine | >99 |

A recent report from our laboratory [see Cancer Research 51:2386 (May 1st 1991) which is incorporated in toto herein] indicates that the compound 3d of the present invention inhibits DNA synthesis due to the inhibition of ribonucleotide reductase activity and inhibition of chain elongation by DNA polymerase α. These inhibitions of the ribonucleotide reductase and DNA polymerase α enzymes by compound 3d were important to the development of the cancerous K562 cells. Although this finding is similar to observations with 9-β-D-arabinofuranosyl-2-fluoroadenine and 2-chloro-2'-deoxyadenosine, the degree of inhibition of these enzymes by the 5'-triphosphate of these nucleoside analogues is quite different. The inhibition of ribonucleoside reductase by 2-chloro-9-(2-deoxy-2-fluoro-β-D-arabinofuranosyl)adenine 5'-triphosphate was the same as that seen with 2-chloro-2'-deoxyadenosine 5'-triphosphate, and the inhibition of DNA polymerase α by 2-chloro-9-(2-deoxy-2-fluoro-β-D-arabinofuranosyl)adenine 5'-triphosphate was similar to that seen with 9-β-D-arabinofuranosyl-2-fluoroadenine 5'-triphosphate. In contrast, 9-β-D-arabinofuranosyl-2-fluoroadenine 5'-triphosphate was a much less potent inhibitor of ribonucleotide reductase than either 2-chloro-2'-deoxyadenosine 5'-triphosphate or 2-chloro-9-(2-deoxy-2-fluoro-β-D-arabinofuranosyl)adenine 5'-triphosphate, and although all of the 2'-deoxyadenosine nucleotide analogues inhibit the incorporation of 2'-deoxyadenosine 5'-triphosphate by DNA polymerase α into the DNA and were more efficient substrates for the polymerase, the incorporation of 2-chloro-2'-deoxyadenosine 5'-monophosphate into DNA by DNA polymerase α did not inhibit the further elongation of the DNA chain to the degree that was seen with the incorporation of either 9-β-D-arabinofuranosyl-2-fluoroadenine 5'-monophosphate or 2-chloro-9-(2-deoxy-2-fluoro-β-D-arabinofuranosyl)adenine 5'-monophosphate. These results indicated that the 2-chloro-9-(2-deoxy-2-fluoro-β-D-arabinofuranosyl)adenine (compound 3d) incorporates properties of both 9-β-D-arabinofuranosyl-2-fluoroadenine and 2-chloro-2'-deoxyadenosine into one compound. Furthermore, in the cell the inhibition of DNA polymerase α by these nucleoside analogues is a function of the ratio of [analogue nucleotide triphosphate] to [2'-deoxyadenosine 5'-triphosphate]. Because 9-β-D-arabinofuranosyl-2-fluoroadenine 5'-triphosphate inhibits ribonucleotide reductase at a 10-fold higher concentration than that required with 2-chloro-9-(2-deoxy-2-fluoro-β-D-arabinofuranosyl)adenine 5'-triphosphate, the 2'-deoxyadenosine 5'-triphosphate pool should be lower and the inhibition of DNA polymerase α should be greater, in cells treated with 2-chloro-9-(2-deoxy-2-fluoro-β-D-arabinofuranosyl)adenine than in cells treated with equimolar concentrations of 9-β-D-arabinofuranosyl-2-fluoroadenine, assuming equal conversion to the triphosphate. These metabolic features may contribute to the potent inhibition of K562 cell growth with compound 3d [2-chloro-9-(2-deoxy-2-fluoro-β-D-arabinofuranosyl)adenine] of the present invention. In addition, the solubility problems associated with the administration of 9-β-D-arabinofuranosyl-2-fluoroadenine should not occur with this compound because of its greater solubility and high potency.

The reason that the 2'-fluorine atom disrupts chain extension is not obvious because the 2'-carbon is not involved in the reaction and a fluorine has an atomic radius slightly larger than a hydrogen atom. Steric hindrance would be expected to be less than is believed to be in the case of arabinofuranosyl nucleotides. It is possible that the electron-withdrawing properties of fluorine may affect the reactivity of the 3'-hydroxyl and/or the three dimensional structure of the DNA chain such that extension of a DNA chain terminated with a 2'-fluoronucleoside by the polymerase is inhibited.

Studies with the P388 leukemia cell line in mice (see Table III) indicate that the most effective compound of the present invention is the compound according to general formula 3d, that is the 2-chloro-2'-fluoro substituted nucleoside. This, coupled with the lower toxicity of the cleavage product, 2-chloroadenine, relative to 2-fluoroadenine, make this compound a preferred compound of the present invention. The following Table III provides a summary of the in vivo activity of the 9-(2-fluoro-2-deoxy-β-D-arabinofuranosyl)-2-haloadenines vs P388 leukemia cell line in which CD2F1 mice were implanted ip with $10^6$ P388 leukemia cells on day 0 in accordance with the protocol of Waud et al [Cancer Res. 50:3232 (1990)].

TABLE III

| Compound | Optimal IP Dose | Schedule | Median % ILS (dying mice only) | Log$_{10}$ change | Tumor-free Survivors |
| --- | --- | --- | --- | --- | --- |
| 3d | 100 | qd 1-5 | +38 | −0.3 | 0/5 |
|  | 200 | qd 1-5 | +59 | −1.6 | 0/3 |
|  | 20 | q 3 h × 8 (Days 1, 5, 9) | +220 | −6.6 | 1/6 |
|  | 25 | q 3 h × 8 (Days 1, 5, 9) | +118 | −2.8 | 0/5 |
| 3g | 100 | qd 1-5 | +63 | −1.8 | 0/3 |
|  | 25 | q 3 h > 8 (Days 1, 5, 9) | +81 | −0.1 | 0/6 |
| 3b | 30 | q 3 h × 8 (Days 1, 5, 9) | +100 | −1.0 | 0/6 |
|  | 50 | q 3 h × 8 (Days 1, 5, 9) | +41 | +1.6 | 0/6 |
|  | 200 | qd 1-5 | +33 | +0.1 | 0/6 |

In the above table, the optimal dose refers to mg/kg/dose ($\leq LD_{50}$); ILS refers to the increase in life span; and the log change refers to the change in viable tumor cell population at the end of therapy compared to that at the start of therapy, based on the median day of death among the animals that died. The data in this table is presented in accordance with the National Cancer Institute activity criteria for drug testing in which an ILS of 20–74% is considered moderate activity, and an ILS of 75% or more is considered good activity.

In addition to the above, the 2,3-dideoxynucleoside depicted as compound 5b showed slight activity against HIV (strain IIIB) in either CEM or MT cell lines in culture.

In a similar test, compound 3d was administered orally and evaluated for antitumor activity against ip P388 leukemia cells. As the data in Table III indicates, the optimal regimen for the compound, administered ip, is in divided doses five on days 1, 5, and 9, a similar schedule was selected for the oral administration of this compound. In this set of experiments, an oral dosage of 67 mg/kg/dose, given q 6 h×4 on days 1, 5, and 9, effected a reduction in tumor burden of 1.7 log$_{10}$ units, a figure which is approximately 2.5 log$_{10}$ units less that that obtained in studies using ip drug administration.

The compounds according to the present invention are useful for their cytotoxic effects, and thus are useful as anticancer compounds in the treatment of cancerous cells in mammals when administered in an amount sufficient to bring about their cytotoxic effect to the desired cancerous cell. The compounds may be administered in a wide range of regimens ranging from about 10 m g to about 1000 mg per day. These regimens may be designed to give the compounds as a single dose or as multiple doses over extended periods of time, and the regimen may be adapted to provide the optimum therapeutic response. For example, several divided doses may be administered daily, or the dose may be proportionally reduced or increased as indicated by the exigencies of the therapeutic situation. The compounds according to the present invention may be administered in the form of the free purine nucleoside or as a nontoxic pharmaceutically acceptable salt thereof, and may be administered either alone or in combination with one or more compounds of the present invention or with additional pharmaceutically active compounds.

The active compounds of the present invention may be administered parenterally, e.g. by subcutaneous, intramuscular, or intravenous injection. Solutions or suspensions of the active compound as a pharmaceutically acceptable salt can be prepared in water or saline containing the appropriate buffers and additives for administration. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability is provided; it must be stable under the conditions of manufacture and storage, and must be preserved against the contaminating action of microorganisms such as bacteria and fungi. The carrier may be a solvent or dispersion medium containing, for example, water, polyol (e.g., glycerol, propylene glycol, and liquid polyethylene glycol), and suitable mixtures thereof. Compositions suitable for intramuscular or subcutaneous injection may also contain minor amounts of salts, acids, and bases to adjust tonicity and buffer the pH.

The compounds according to the present invention may also be suitable for oral administration, for example with an inert diluent or with an assimilable edible carrier, or they may be enclosed in hard or soft shell gelatin capsules, or compressed into tablets. For oral therapeutic administration, the compounds may be incorporated with excipients commonly used in the formulation of oral pharmaceutical preparations as, for example, sweetening agents, and preservatives.

In addition, the compounds of the present invention may be formulated in accordance with acceptable pharmaceutical formulation techniques for administration by other routes such as administration within topical ointments, creams or salves, as suppositories, or as lozenges.

Thus, while we have illustrated and described the preferred embodiment of our invention, it is to be understood that this invention is capable of variation and modification and we therefore do not wish to be limited to the precise terms set forth, but desire to avail ourselves of such changes and alterations which may be made for adapting the invention to various usages and conditions. Among such variations and modifications are, for example, and without limitation, the use of pharmaceutically acceptable salts of the disclosed purine nucleosides which may be designed for providing the purine nucleosides according to the present invention to a cell susceptible to cytotoxicity, to any minor substitution on the active nucleoside according to the present invention which results in no untoward effects upon the activity of the modified nucleoside from that of the depicted purine nucleosides or which results in the same or substantially the same activity as that found in the purine nucleosides depicted in accordance with the preceding disclosure; changes in formulation made due to the specific route of administration of the nucleosides according to the present invention; and changes made to the nucleoside molecule or composition formulation because of a specific salt form of the nucleoside according to the present invention. Accordingly, such changes, alterations and modifications are properly intended to be within the full range of equivalents, and therefore within the purview of the following claims.

Having thus described our invention and the manner and process of making and using the same in such full, clear, concise, and exact terms so as to enable any person skilled in the art to which it pertains, or with which it is most nearly connected, to make and use the same.

We claim:

1. A pharmaceutical composition comprising a compound of the formula

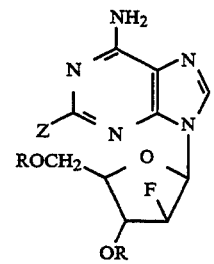

wherein R, each which may be the same or different, is hydrogen or a protecting group; wherein Z is a halogen of the group F, Cl, and Br; and pharmaceutically acceptable salts thereof, said composition being in combination with a pharmaceutically acceptable carrier for oral, topical, or parenteral administration.

2. A pharmaceutical composition according to claim 1 wherein R is a protecting group.

3. A pharmaceutical composition according to claim 1 wherein R is hydrogen.

4. A pharmaceutical composition according to claims 1, 2 or 3 wherein Z is Cl.

5. A pharmaceutical composition according to claim 1 wherein the compound is 2-Chloro-9-(2-deoxy-2-fluoro-β-D arabinofuranosyl)-9H-purin-6-amine.

6. A purine nucleoside having the formula

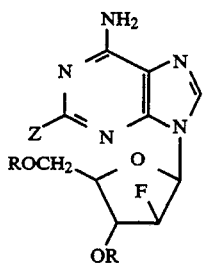

wherein R, each which may be the same or different, is hydrogen or a protecting group; wherein Z is a halogen of the group F, Cl, and Br; and pharmaceutically acceptable salts thereof.

7. A purine nucleoside according to claim 6 wherein R is hydrogen.

8. A purine nucleoside according to claim 6 wherein R is a protecting group.

9. A purine nucleoside according to claims 6, 7 or 8 wherein Z is Cl.

10. A purine nucleoside according to claim 6 which is 2-Chloro-9-(2-deoxy-2-fluoro-β-D arabinofuranosyl)-9H-purin-6-amine.

* * * * *